United States Patent [19]

Britton

[11] Patent Number: 5,148,815
[45] Date of Patent: Sep. 22, 1992

[54] SPINAL RESTRAINT DEVICE

[76] Inventor: Douglas Britton, #203, 10835-115 Street, Edmonton, Alberta, Canada, T5H 3L2

[21] Appl. No.: 672,827

[22] Filed: Mar. 21, 1991

[30] Foreign Application Priority Data

Jun. 6, 1990 [CA] Canada .................. 2018744

[51] Int. Cl.⁵ .............................................. A61F 5/37
[52] U.S. Cl. .................................. 128/869; 128/870; 128/876
[58] Field of Search .............. 128/869, 870, 871, 875, 128/876; 297/484, 486

[56] References Cited

U.S. PATENT DOCUMENTS

| | | | |
|---|---|---|---|
| 914,785 | 3/1909 | Boyce . | |
| 2,195,334 | 3/1940 | Lethern | 297/484 |
| 2,758,769 | 8/1956 | Nunn et al. | 297/484 X |
| 2,817,393 | 12/1957 | Mitchell | 297/484 X |
| 3,275,373 | 9/1966 | Card | 297/389 |
| 3,458,878 | 8/1969 | Combs | 128/876 X |
| 3,779,599 | 12/1973 | Gottfried | 297/484 X |
| 3,889,668 | 6/1975 | Ochs et al. | 128/134 |
| 3,954,280 | 5/1976 | Roberts et al. | 297/484 X |
| 4,127,120 | 11/1978 | Applegate | 128/870 |
| 4,402,548 | 9/1983 | Mason | 297/464 |
| 4,794,656 | 1/1989 | Henley, Jr. | 5/82 R |
| 4,841,961 | 6/1989 | Burlage et al. | 128/876 |
| 5,014,374 | 5/1991 | Williams | 128/876 X |

FOREIGN PATENT DOCUMENTS 1350503 12/1963 France .................. 128/875

OTHER PUBLICATIONS

Article "Type" 'ZB' Restraint Harness General Information, pp. 1-6.
Driving in Competition, Alan Johnson, W. W. Norton and Company, 1976.
Cars and Car Conversions, Dec. issue (photograph only).

Primary Examiner—Robert A. Hafer
Assistant Examiner—Sam Rimell
Attorney, Agent, or Firm—Beveridge, DeGrandi & Weilacher

[57] ABSTRACT

A spinal restraint device and a method of securing a patient to a spinal restraint device are described. The spinal restraint device consists of a spine board, having a plurality of strap mounting openings. A plurality of straps are mounted to the openings in the spineboard. At least one yoke is provided. The yoke has a first strap which extends through the yoke from a mounting opening on the spineboard above the yoke and a second strap which extends through the yoke from a mounting opening on the spineboard below the yoke. The first strap and second strap describe the shape of an hourglass.

7 Claims, 3 Drawing Sheets

SPINAL RESTRAINT DEVICE

The present invention relates to a spinal restraint device and a method of securing a patient to a spinal restraint device.

BACKGROUND OF THE INVENTION

Spinal restraint devices presently used by paramedics consist of spine boards in combination with a plurality of straps for use in securing a patient to the spine board. A variety of strap configurations have been tried. Some strap configurations are very effective at preventing movement of a patient, but bring pressure to bear on vital areas such as the rib cage or the abdomen. Other strap configurations distribute the force of the straps to ensure undue pressure is not brought to bear upon vital areas, but are not very effective at preventing movement of the patient. Both movement of the patient and undue pressure on vital areas are viewed as undesirable.

This can be further illustrated with reference to spinal restraint devices which are commercially available. Straps configured to form an "X" are among the most effective at preventing movement of the patient. However, the pressure of the straps forming the "X" upon the rib cage can impede breathing and this configuration is not advisable for pregnant women. The "spider" configuration of straps, as illustrated in U.S. Pat. No. 4,841,961, is among the most effective in ensuring undue pressure in not brought to bear upon vital areas. However, some movement of the patient frequently occurs when the spine board is turned sideways to permit the patient to vomit or is placed on end when going down stairs.

SUMMARY OF THE INVENTION

What is required is a spinal restraint device which permits the patient to be securely fastened to a spine board without placing pressure on vital areas.

According to the present invention there is provided a spinal restraint device which is comprised of a spine board, having a plurality of strap mounting means. A plurality of straps are mounted to the spineboard by strap mounting means. At least one yoke is provided. A first strap extends through the yoke from strap mounting means on the spineboard above the yoke. A second strap extends through the yoke from strap mounting means on the spineboard below the yoke. The first strap and second strap describe the shape of an hourglass.

According to another aspect of the invention there is provided a method of securing an upper body of a patient to a spinal restraint device which consists of a spine board with a plurality of strap mounting means, a plurality of straps mounted to the spineboard, and at least one yoke. The method is comprised of the following steps. Place a yoke in the vicinity of a sternum of a patient. Extend a strap from mounting means on a first side of the patient down across a first clavicle, through the yoke, up across a second clavicle, to mounting means on a second side of the patient. Extend a strap from mounting means on the first side in the vicinity of a patient's waist, up through the yoke and back down to mounting means on the second side in the vicinity of the patient's waist. The straps describe the shape of an hourglass and the force of each strap bears upon the patient's sternum.

With the described method the force of the straps bears upon the patient's sternum. The sternum can withstand substantially more pressure than is possible with other strap configurations without impeding the patient's breathing. It also leaves the abdomen substantially free, so it can be used with pregnant women. Monitors, such as defibrillators, can be used without removing the straps.

According to another aspect of the invention there is provided a method of securing a lower body of a patient to a spinal restraint device consisting of a spine board with a plurality of strap mounting means, a plurality of straps mounted to the spineboard, and at least one yoke. The method is comprised of the following steps. Place a yoke in the vicinity of a symphysis pubis of the patient. Extend a strap from mounting means on a first side of the patient down across a first iliac crest, through the yoke, up across a second iliac crest, to mounting means on a second side of the patient. Extend a strap from mounting means on the first side of the patient in the vicinity of a first patella, up across a first femur, through the second yoke, down across a second femur to mounting means on the second side of the patient in the vicinity of a second patella. The straps describe the shape of an hourglass with the force of one strap bearing upon the patient's iliac crests, and the force of the other strap bearing upon the patient's femurs.

With the described method most of the force of the straps is born by the iliac crests of the patient. The patient's pelvis is tightly secured to the spine board permitting the spine board to be turned on its side without having the patient move sideways.

Although beneficial results may be obtained through use of one or both of the described methods, even more beneficial results may be obtained by extending a strap from mounting means on the first side of the patient, wrapping the strap around the patient's ankles in the form of a figure "8", and extending the strap transversely across the spine board to mounting means on the second side of the patient.

With the figure "8" configuration, the spine board can be placed on end without fear of the patient moving longitudinally on the spine board.

BRIEF DESCRIPTION OF THE DRAWINGS

These and other features of the invention will become more apparent from the following description in which reference is made to the appended drawings, wherein.

DETAILED DESCRIPTION OF THE PREFERRED EMBODIMENT

Figure 2:
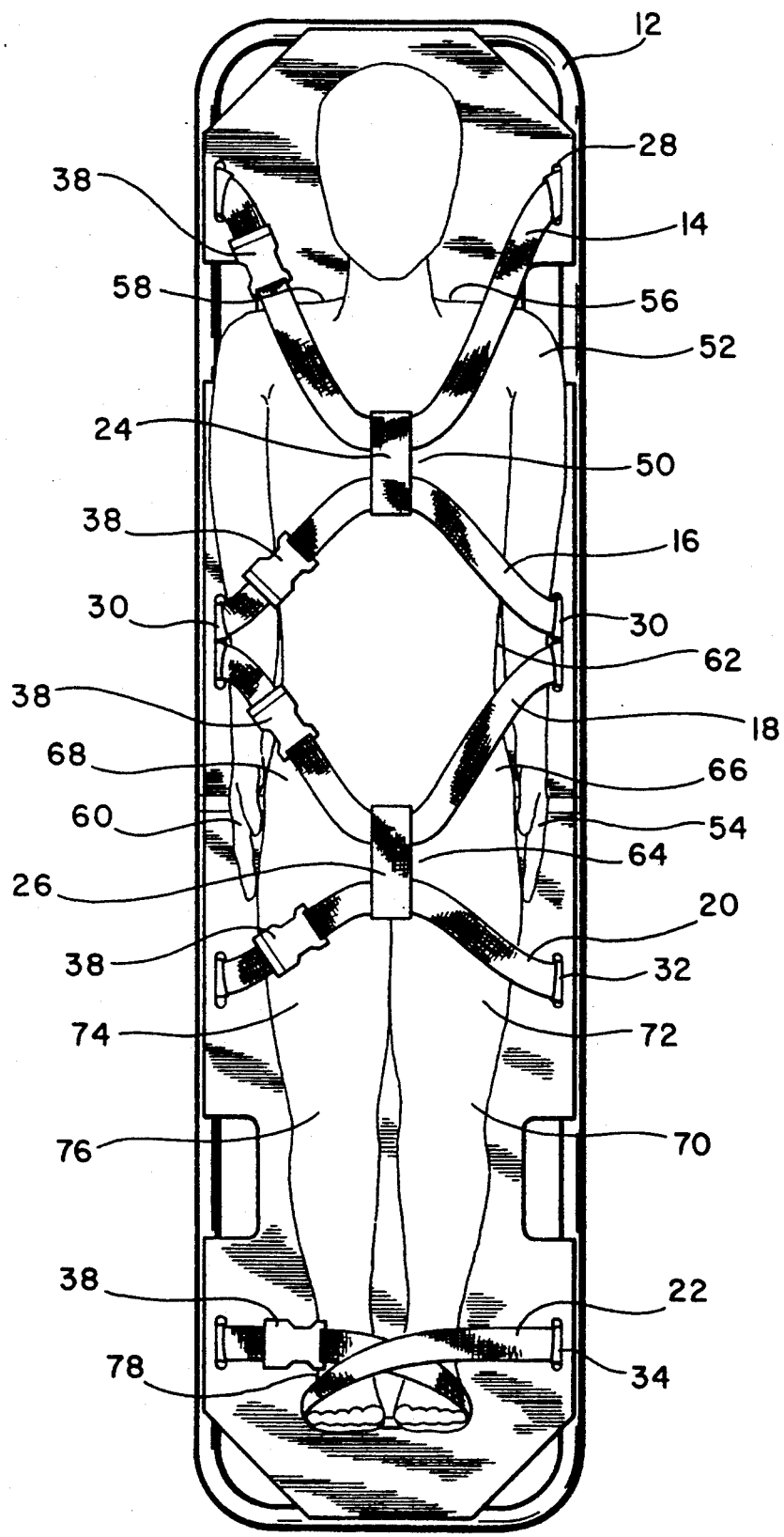
FIG. 2 is a top plan view of a patient secured to the spinal restraint device illustrated in FIG. 1.
Figure 3:
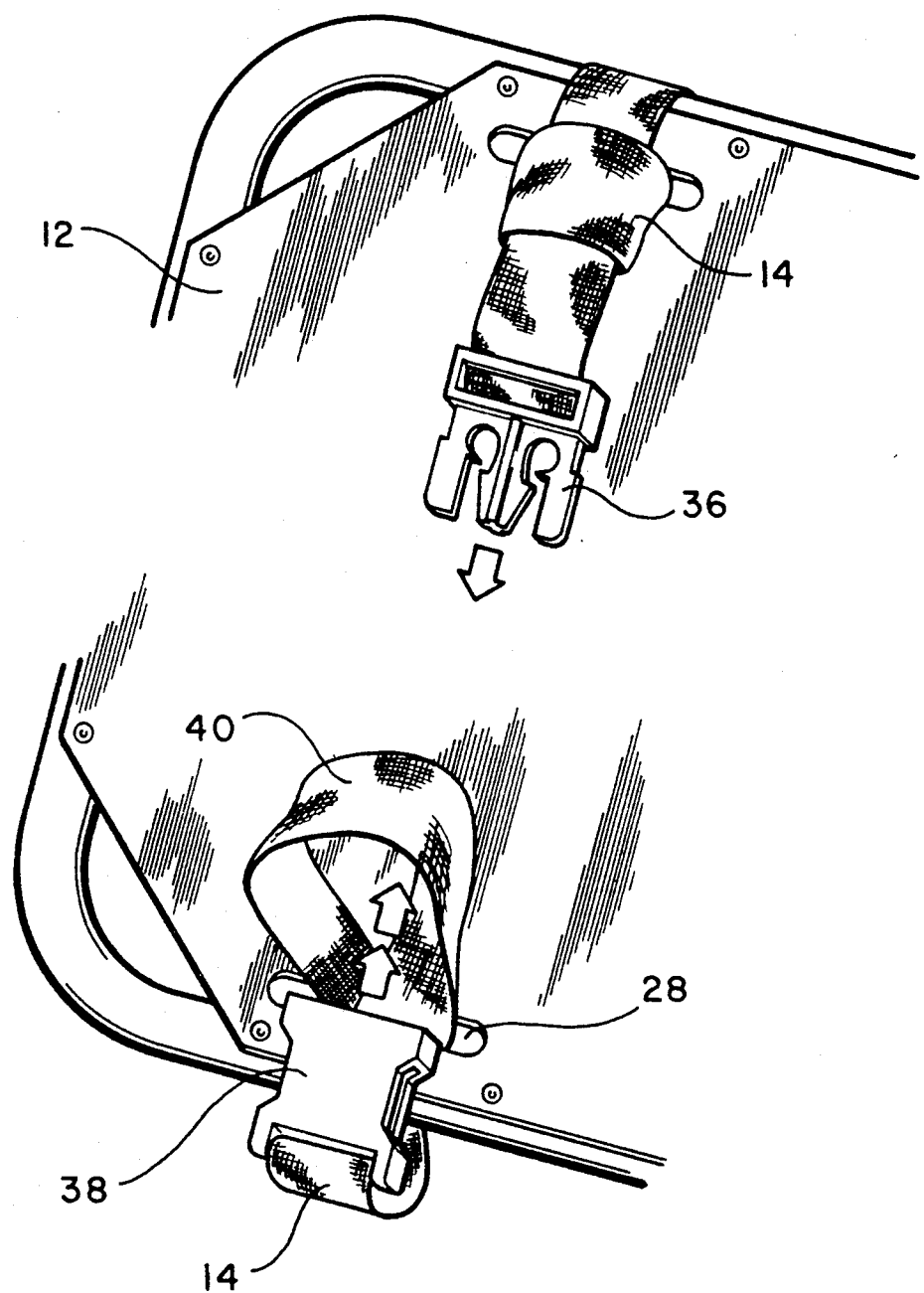
FIG. 3 is a detailed view of a portion of the spinal restraint device illustrated in FIG. 1.

The preferred embodiment will now be described with reference to FIGS. 1 through 3. The preferred embodiment, generally designated by reference numeral 10, is a spinal restraint device. The primary components of spinal restraint device 10 are a spine board 12, a plurality of straps, 14, 16, 18, 20, and 22, and yokes 24 and 26.

Figure 1:
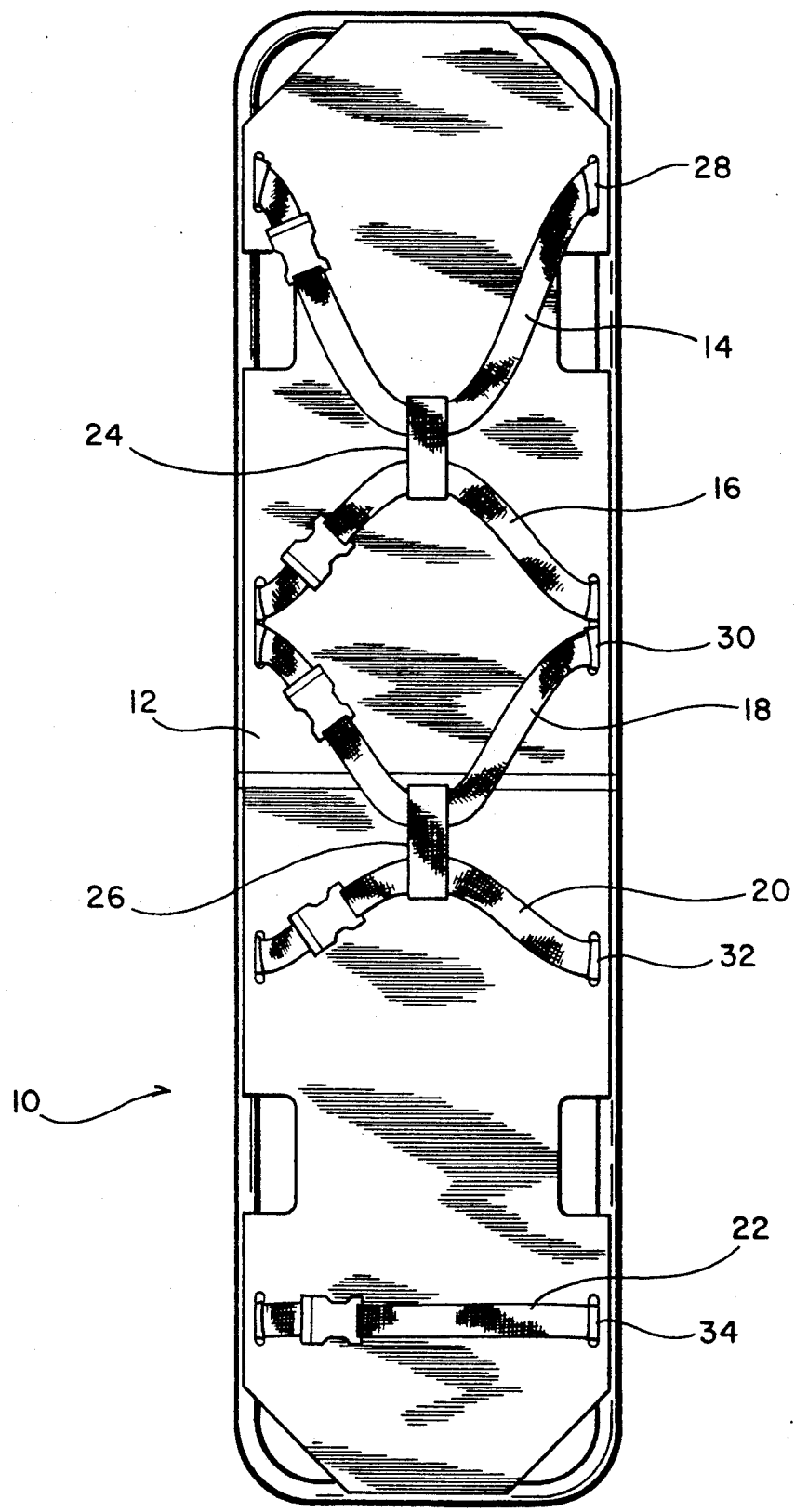
FIG. 1 is a top plan view of a preferred embodiment of the invention.

Referring to FIG. 1, spine board 12 has a plurality of pairs of openings 28, 30, 32, and 34 along its periphery which serve as strap mounting means. Each of straps 14, 16, 18, 20 and 22 are mounted to one of openings 28 along the periphery of spineboard 12. Strap 14 extends through yoke 24 from opening 28 on spineboard 12 which is positioned above yoke 24. Strap 16 extends through yoke 24 from opening 30 on spineboard 12 below yoke 24. Strap 14 and strap 16 describe the shape of an hourglass. Strap 18 extends through yoke 26 from opening 30 on spineboard 12 which is positioned above yoke 26. Strap 20 extends through yoke 26 from opening 32 on spineboard 12 below yoke 26. Strap 18 and strap 20 describe the shape of an hourglass. Strap 22 is secured to opening 34. Referring to FIG. 3, each of the straps has a male connection end 36, and a female connection end 38. Female connection end 38 is anchored to spine board 12, by forming a loop 40 in the strap, extending loop 40 through one of the openings in spine board 12 and inserting female connection end 38 through loop 40.

Most ambulance authorities already have spine board 12; as the unique aspect of spinal restraint device 10 is it's strap configuration. This is called the "hour glass" configuration for reasons which will become apparent. The straps necessary to follow the teachings of the invention are, therefore, sold in the form of a kit which consists of one yoke 24 and two straps 14 and 16; or two yokes 24 and 26 with four straps 14, 16, 18, and 20.

The advantages provided by spinal restraint device 10 will become apparent with the following description of the recommended method of securing a patient to a spinal restraint device. The method which will hereinafter be described requires that a spinal restraint device, such as identified by reference numeral 10, be used. The method consists of the following steps, described with reference to FIG. 2.

The upper body of the patient is secured as follows. Place a first yoke 24 in the vicinity of a sternum 50 of a patient 52. Extend a first strap 14 from opening 28 on a first side 54 of patient 52 down across a first clavicle 56, through yoke 24, up across a second clavicle 58, to connection 38 at opening 28 on a second side 60 of patient 52. Extend a second strap 16 from opening 30 on the first side 54 in the vicinity of a patient's waist 62, up through yoke 24 and back down to connection 38 at opening 30 on second side 60 in the vicinity of patient's waist 62. It is to be noted that first strap 14 and second strap 16 describe the shape of an hourglass; hence the reference to "hour glass" strap configuration. The force of straps 14 and 16 bear upon patient's sternum 50.

With the described method the force of the straps bears upon the patient's sternum. The sternum can withstand substantially more pressure than is possible with other strap configurations without impeding the patient's breathing; the straps can therefore be tightened to a greater extent. It also leaves the abdomen substantially free, so it can be used with pregnant women. Monitors, such as defibrillators, can be used without removing the straps. If desired, the arms of the patient can be restrained.

The lower body of a patient is secured as follows. Place a second yoke 26 in the vicinity of a symphysis pubis 64 of the patient 52. Extend a third strap 18 from opening 30 on first side 54 of patient 52, down across a first iliac crest 66, through yoke 26, up across a second iliac crest 68, to connection 38 at opening 30 on second side 60 of patient 52. Extend a fourth strap 20 from opening 32 on first side 54 of patient 52 in the vicinity of a first patella 70, up across a first femur 72, through second yoke 26, down across a second femur 74 to connection 38 at opening 32 on second side 60 of patient 52 in the vicinity of a second patella 76. It is to be noted that third strap 18 and fourth strap 20 describe the shape of an hourglass. The force of third strap 18 bears upon the patient's iliac crests 66 and 68. The force of fourth strap 20 bears upon the patient's femurs 72 and 74.

With the described method most of the force of the straps is born by the iliac crests of the patient. The patient's pelvis is tightly secured to the spine board permitting the spine board to be turned on its side without having the patient move sideways. The legs of the patient are confined, preventing an aggressive patient from kicking.

The method of securing the lower legs of the patient is as follows. Extend a fifth strap 22 from opening 34 on first side 54 of patient 52. Wrap strap 22 around a patient's ankles 78 to form a figure "8". Extend strap 22 transversely across spine board 12 to connection 38 at opening 34 on second side 60 of patient 52.

With this method the patient is prevented from sliding longitudinally in relation to the spine board. The figure "8" permits the spine board to be placed on end without concern about the patient sliding down. This is particularly useful when operating in confined spaces or taking a patient up or down an incline.

It will be apparent to one skilled in the art that spinal restraint device 10, as described, together with the method for securing a patient to spinal restraint device 10 represent an advance in the art. A patient can be securely fastened to spinal restraint device 10, without placing undue pressure upon the patient's vital areas. It will also be apparent to one skilled in the art that modifications may be made to the preferred embodiment without departing from the spirit and scope of the invention. For example, the Applicant prefers to sew a seam along the mid-point of yokes 24 and 26 to separate the straps. A variety of different yoke configurations would work equally well.

The embodiments of the invention in which an exclusive property or privilege is claimed are defined as follows:

1. A spinal restraint device, comprising:
   a. a spine board, having a plurality of strap mounting means;
   b. a plurality of straps mounted to the spineboard by said strap mounting means; and
   c. at least one yoke
   d. said plurality of straps including a first strap which extends through the yoke from strap mounting means positioned on the spineboard above the yoke to strap mounting means on an opposite side of said spineboard, and said plurality of straps including a second strap which extends through the yoke from strap mounting means on the spineboard positioned below the yoke to strap mounting means on an opposite side of said spineboard, such that the first strap and second strap describe the shape of an hourglass.

2. A method of securing a patient to a spinal restraint device having a spine board with a plurality of strap mounting means, a plurality of straps mounted to the spineboard, and at least one yoke, comprising the steps of:
   a. placing a yoke in the vicinity of a sternum of a patient;
   b. extending a strap from mounting means on a first side of the patient down across a first clavicle, through the yoke, up across a second clavicle, to mounting means on an opposite side of the patient;
   c. extending a strap from mounting means on the first side in the vicinity of a patient's waist, up through the yoke and back down to mounting means on the opposite side in the vicinity of the patient's waist, such that the straps describe the shape of an hourglass and the force of each strap bears upon the patient's sternum; and d. securing a lower body of the patient to the spine board with straps.

3. A method of securing a patient to a spinal restraint device having a spine board with a plurality of strap mounting means, a plurality of straps mounted to the spineboard, and at least one yoke, comprising the steps of:

a. securing an upper body of a patient to the spineboard with straps;

b. placing a yoke in the vicinity of a symphysis pubis of the patient;

c. extending a strap from mounting means on a first side of the patient down across a first iliac crest, through the yoke, up across a second iliac crest, to mounting means on an opposite side of the patient;

d. extending a strap from mounting means on the first side of the patient in the vicinity of a first patella, up across a first femur, through the second yoke, down across a femur to mounting means on the opposite side of the patient in the vicinity of a second patella, such that the straps describe the shape of an hourglass with the force of one strap bearing upon the patient's iliac crests, and the force of the other strap bearing upon the patient's femurs.

4. A method of securing a patient to a spineboard as defined in claim 3, including the further step of taking a strap from mounting means on the first side of the patient, wrapping the strap around the patient's ankles in the form of a figure "8", and extending the strap transversely across the spineboard to mounting means on the second side of the patient.

5. A method of securing a patient to a spineboard as defined in claim 2, including the further step of taking a strap from mounting means on the first side of the patient, wrapping the strap around the patient's ankles in the form of a figure "8", and extending the strap transversely across the spine board to mounting means on the second side of the patient.

6. A method of securing a patient to a spinal restraint device having a spine board with a plurality of strap mounting means, a plurality of straps mounted to the spineboard, and at least one yoke, comprising the steps of:

a. placing a first yoke in the vicinity of a sternum of a patient;

b. extending a first strap from mounting means on a first side of the patient down across a first clavicle, through the yoke, up across a second clavicle, to mounting means on a second side of the patient;

c. extending a second strap from mounting means on the first side in the vicinity of a patient's waist, up through the yoke and back down to mounting means on the second side in the vicinity of the patient's waist, such that the first strap and the second strap describe the shape of an hourglass and the force of each strap bears upon the patient's sternum;

d. placing a second yoke in the vicinity of a symphysis pubis of the patient;

e. extending a third strap from mounting means on a first side of the patient down across a first iliac crest, through the yoke, up across a second iliac crest, to mounting means on a second side of the patient;

f. extending a fourth strap from mounting means on the first side of the patient in the vicinity of a first patella, up across a first femur, through the second yoke, down across a second femur to mounting means on the second side of the patient in the vicinity of a second patella, such that the third strap and the fourth strap describe the shape of an hourglass with the force of the third strap bearing upon the patient's iliac crests, and the force of the fourth strap bearing upon the patient's femurs; and g. extending a fifth strap from mounting means on the first side of the patient, wrapping the strap around the patient's ankles in the form of a figure "8", and extending the strap transversely across the spine board to mounting means on the second side of the patient.

7. A method of securing a patient to a spinal restraint device having a spine board with a plurality of strap mounting means, a plurality of straps mounted to the spineboard, and at least one yoke, comprising the steps of:

a. placing a first yoke in the vicinity of a sternum of a patient;

b. extending a first strap from mounting means on a first side of the patient down across a first clavicle, through the yoke, up across a second clavicle, to mounting means on a second side of the patient;

c. extending a second strap from mounting means on the first side in the vicinity of a patient's waist, up through the yoke and back down to mounting means on the second side in the vicinity of the patient's waist, such that the first strap and the second strap describe the shape of an hourglass and the force of each strap bears upon the patient's sternum;

d. placing a second yoke in the vicinity of a symphysis pubis of the patient;

e. extending a third strap from mounting means on a first side of the patient down across a first iliac crest, through the yoke, up across a second iliac crest, to mounting means on the second side of the patient, and f. extending a fourth strap from mounting means on the first side of the patient in the vicinity of a first patella, up across a first femur, through the second yoke, down across a second femur to mounting means on the second side of the patient in the vicinity of the second patella, such that the third strap and the fourth strap describe the shape of an hourglass with the force of the third strap bearing upon the patient's iliac crests, and the force of the fourth strap bearing upon the patient's femurs.

* * * * *